US012240984B2

(12) United States Patent
Albenge et al.

(10) Patent No.: US 12,240,984 B2
(45) Date of Patent: Mar. 4, 2025

(54) PROCESS FOR PREPARING AN AQUEOUS GEL INK WITH FIXED COLOR COMPRISING SILVER OR GOLD NANOPARTICLES

(71) Applicants: SOCIETE BIC, Clichy (FR); UNIVERSITE DE HAUTE ALSACE, Mulhouse (FR); CENTRE NATIONAL DE LA RECHERCHE SCIENTIFIQUE, Paris (FR)

(72) Inventors: Olivier Albenge, Clichy (FR); Romain Metillon, Clichy (FR); Karine Mougin, Paris (FR); Feriel Ghellal, Clichy (FR); Arnaud Spangenberg, Mulhouse (FR)

(73) Assignees: SOCIETE BIC, Clichy (FR); UNIVERSITÉ DE HAUTE-ALSACE, Mulhouse (FR); CENTRE NATIONAL DE LA RECHERCHE SCIENTIFIQUE, Paris (FR)

( * ) Notice: Subject to any disclaimer, the term of this patent is extended or adjusted under 35 U.S.C. 154(b) by 569 days.

(21) Appl. No.: 17/632,135

(22) PCT Filed: Aug. 28, 2020

(86) PCT No.: PCT/EP2020/074119
§ 371 (c)(1),
(2) Date: Feb. 1, 2022

(87) PCT Pub. No.: WO2021/038066
PCT Pub. Date: Mar. 4, 2021

(65) Prior Publication Data
US 2022/0275229 A1    Sep. 1, 2022

(30) Foreign Application Priority Data

Aug. 29, 2019  (EP) ..................... 19306055

(51) Int. Cl.
| C09D 11/17 | (2014.01) |
| B22F 9/24 | (2006.01) |
| B82Y 30/00 | (2011.01) |
| B82Y 40/00 | (2011.01) |
| C07C 69/618 | (2006.01) |
| C08K 3/08 | (2006.01) |

(52) U.S. Cl.
CPC ............. C09D 11/17 (2013.01); B22F 9/24 (2013.01); C07C 69/618 (2013.01); *B82Y 30/00* (2013.01); *B82Y 40/00* (2013.01); *C08K 2003/0806* (2013.01); *C08K 2003/0831* (2013.01)

(58) Field of Classification Search
CPC ... C09D 11/16–20; B82Y 30/00; B82Y 40/00; B22F 9/24; B22F 9/245; C08K 2003/0806; C08K 2003/0831
See application file for complete search history.

(56) References Cited

U.S. PATENT DOCUMENTS

| 8,870,998 | B2 | 10/2014 | Nolte et al. |
| 2005/0204956 | A1 | 9/2005 | Berkei et al. |
| 2009/0214766 | A1 | 8/2009 | Magdassi et al. |

FOREIGN PATENT DOCUMENTS

| CN | 1777653 A | 5/2006 |
| CN | 101027151 A | 8/2007 |
| CN | 101128550 A | 2/2008 |
| CN | 102202815 A | 9/2011 |
| CN | 105891501 A | 8/2016 |
| CN | 106795064 A | 5/2017 |
| CN | 106867315 A | 6/2017 |
| CN | 107022241 A | 8/2017 |
| CN | 108372307 A | 8/2018 |
| CN | 110167885 A | 8/2019 |
| EP | 0837113 B1 | 12/2004 |
| EP | 3385342 A1 | 10/2018 |
| JP | 2004067931 A | 3/2004 |
| JP | 2008297323 A | 12/2008 |
| JP | 2012057205 A | 3/2012 |
| JP | WO2012057205 A1 | 5/2014 |
| WO | 2006072959 A1 | 7/2006 |
| WO | WO-2014109459 A1 * | 7/2014 ........... A61K 9/0009 |

OTHER PUBLICATIONS

Partial machine translation of WO-2014109459-A1 (Year: 2014).*
International Search Report and Written Opinion in International Application No. PCT/EP2020/074119, mailed Nov. 19, 2020 (10 pages).
First Search issued in corresponding CN application No. 202080054286, issued Dec. 26, 2022.

* cited by examiner

*Primary Examiner* — Kregg T Brooks
(74) *Attorney, Agent, or Firm* — Bookoff McAndrews, PLLC

(57) ABSTRACT

The invention relates a process for preparing an aqueous gel ink with fixed color comprising the following steps: (i) preparing a gel-based matrix of aqueous ink; (ii) preparing an aqueous suspension of gold or silver nanoparticles with a fixed color; (iii) adding the aqueous suspension of gold or silver nanoparticles obtained in step (ii) to the gel-based matrix of aqueous ink obtained in step (i).

19 Claims, No Drawings

PROCESS FOR PREPARING AN AQUEOUS GEL INK WITH FIXED COLOR COMPRISING SILVER OR GOLD NANOPARTICLES

CROSS-REFERENCE TO RELATED APPLICATIONS

This application is the U.S. national phase entry under 35 U.S.C. § 371 of International Application No. PCT/EP2020/074119, filed Aug. 28, 2020, which claims priority to European Patent Application No. 19306055.5, filed Aug. 29, 2019, the entire contents of which are incorporated herein by reference.

FIELD OF THE INVENTION

The present invention relates to a process for preparing an aqueous gel ink with fixed color comprising silver or gold nanoparticles, and to an aqueous gel ink obtainable by said process, which ink is free from any dye and pigment, and to a writing instrument comprising said aqueous gel ink with fixed color.

BACKGROUND OF THE INVENTION

U.S. Pat. No. 8,870,998 discloses a process for producing metal nanoparticles wherein through a reduction process, metal ions are reduced by means of at least one reducing agent in the presence of at least one polymeric stabilizer having a weight-average molecular weight of at least 1,000 g/mol. The reducing agent is one of inorganic hydrides; inorganic thiosulfates or thiosulfuric acid; inorganic sulfides or hydrogen sulfide; inorganic sulfites; hydrazines; hydroxylamines; hydrogen; carbon monoxide; acetylene; oxalic acid or oxalates; citric acid or citrates; tartaric acid or tartrates; mono or polyhydric alcohols; sugars; and inorganic phosphides.

WO 2006/072959 discloses a method for preparing an aqueous-based dispersion of metal nanoparticles comprising: (i) providing an aqueous suspension of a metal salt, (ii) pre-reducing said metal salt suspension by a water-soluble polymer capable of metal reduction to from metal nuclei, and (iii) adding a chemical reducer to form metal nanoparticles in dispersion. The chemical reducer is selected from trisodium citrate, ascorbic acid, disodium tartrate, hydrazine and sodium borohydride.

JP-A-2008297323 discloses an ink composition suitable for writing, which comprises a dispersion of metal nanoparticles coated with a protective colloid and a solvent, wherein the protective colloid is selected from oxygen or nitrogen atom-containing vinyl polymers, carboxylic acids and thiols. The metal nanoparticles are obtained by treatment of a metal salt with a reducing agent such as sodium borohydride.

One of the objectives of the present invention is to replace all type of dyes and pigments normally present in aqueous gel inks, which have the disadvantage of being expensive and causing high production costs. Another objective of the present invention is to replace all types of dyes and pigments normally present in aqueous gel inks, which have the disadvantage of being irritating to biological membranes, for example skin and eyes, and may cause allergies. Another objective of the present invention is to avoid to the extent possible using toxic or corrosive reagents when preparing the aqueous gel ink.

To this end, the inventors have developed a specific process through which it is possible to obtain UV light-resistant aqueous gel inks with fixed color by replacing dyes and pigments in conventional aqueous gel inks with metal nanoparticles. The process includes preparing a dispersion of metal nanoparticles using a specific reducing agent, which avoids having to use a stabilizer, e.g. a polymer stabilizer, or having to coat the nanoparticles during their synthesis. Moreover, the process of the invention is performed at low temperature ranges, works in an ecologically viable manner, and also takes account of ecological requirements.

SUMMARY OF THE INVENTION

The present invention relates to a process for preparing an aqueous gel ink with fixed color comprising the following steps:
(i) preparing a gel-based matrix of aqueous ink;
(ii) preparing an aqueous suspension of gold or silver nanoparticles with fixed color by mixing gold or silver salts with:
water,
a derivative of alkaline earth metal,
an ester of retinol of formula (I):

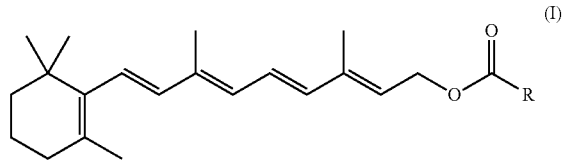

wherein R is an optionally substituted $C_1$-$C_6$ aliphatic group, specifically a ($C_1$-$C_6$)alkyl group, and
optionally, a carbonate;
(iii) adding under stirring the aqueous suspension of gold or silver nanoparticles obtained in step (ii) to the gel-based matrix of aqueous ink obtained in step (i), thereby obtaining an aqueous gel ink with fixed color with gold or silver nanoparticles dispersed therein.

The invention also relates to the aqueous gel ink with fixed color obtainable by the above-mentioned process, comprising gold or silver nanoparticles dispersed therein.

The invention also relates to the use of the aqueous gel ink of fixed color as defined above for writing onto an absorbing support.

The invention also relates to a writing instrument comprising (i) an axial barrel containing an aqueous gel ink with fixed color as defined above and (ii) a pen body which delivers the aqueous gel ink stored in the axial barrel.

The process according to the invention enables to obtain an aqueous ink composition which exhibits a plasmon effect (also called plasmonic effect). Hence, different plasmonic color of the composition can be obtained depending on the content of the components used.

Plasmonic color is due to the light absorption by silver or gold nanoparticles and/or the spacing between them in the composition.

Depending on their size, shape, and distance, the color of the dispersion of the gold or silver nanoparticles can change, as well as its properties. This is due to the plasmon resonance. The exposure of the gold or silver nanoparticles to a certain frequency of waves brings the electrons to gather in a certain place, which changes in accordance with the size and shape of the gold or silver nanoparticles. This agglomeration of electrons provokes an anisotropy of the gold or silver nanoparticles, which will then lead to a change of light absorption and scattering, resulting in a specific color. Plasmon resonance is also affected by the distance between the gold or silver nanoparticles due to the coupling of said gold or silver nanoparticles. Indeed, the closer the gold or silver nanoparticles are, the more they will interact with each other, which will increase their coupling effect also called plasmon effect. In the same way, the shape influences the plasmon resonance.

DETAILED DESCRIPTION OF THE INVENTION

In one aspect, the present invention relates to a process for preparing an aqueous ink with fixed color comprising the following steps:

(i) preparing a matrix of aqueous ink, more specifically a gel-based matrix;

(ii) preparing an aqueous suspension of gold or silver nanoparticles with fixed color by mixing gold or silver salts with:
water,
a derivative of alkaline earth metal,
an ester of retinol of formula (I):

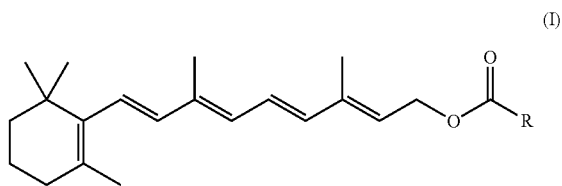

(I)

wherein R is an optionally substituted $C_1$-$C_6$ aliphatic group, specifically a ($C_1$-$C_6$)alkyl group, and
optionally, a carbonate;

(iii) adding under stirring the aqueous suspension of gold or silver nanoparticles obtained in step (ii) to the matrix of aqueous ink, more specifically an aqueous gel ink, obtained in step (i), thereby obtaining an aqueous ink, more specifically an aqueous gel ink, with fixed color with gold or silver nanoparticles dispersed therein.

For the purposes of the present invention, the term "ink" is intended to mean a "writing ink" i.e. an ink intended to be used in a writing instrument, and in particular in a pen. A writing ink should not be confused with a "printing ink" which is used in printing machines and which does not have the same technical constraints and thus the same specifications. Indeed, a writing ink must not contain solid particles the size of which is greater than the channels of the writing instrument, in order to avoid blocking them, which would inevitably lead to writing being irreversibly stopped. In addition, it must allow an ink flow rate suitable for the writing instrument used, in particular a flow rate of between 100 and 500 mg/200 m of writing, and specifically between 150 and 400 mg/200 m of writing. The ink must also dry sufficiently rapidly to avoid smudging the writing medium. The ink must also avoid the problems of migration (bleeding) over time.

In addition, a "writing ink" must not be too fluid, so as to avoid leaks during writing. However, it must be sufficiently fluid to facilitate the flow of the writing action.

In the particular case of the invention, the writing ink can be more specifically a "gel ink" (which corresponds therefore to a thixotropic ink), in particular the viscosity measured at rest (at a shear rate of 0.01 $s^{-1}$) at 20° C. is different and in particular higher than the viscosity measured with a shear rate of 5,000 $s^{-1}$ at 20° C. using the same rheometer such as a cone-and-plate rheometer for example Malvern KINEXUS with a cone of 60 mm and an angle of 1°. In a particular embodiment, the viscosity of the gel ink according to the present invention measured under these conditions ranges from 1,000 to 7,000 mPa·s, specifically from 2,000 to 5,000 mPa·s, and more specifically from 2,500 to 3,500 mPa·s, with a shear rate of 1 $s^{-1}$, and specifically from 5 to 50 mPa·s, more specifically from 7 to 40 mPa·s, and still more specifically from 10 to 20 mPa·s with a shear rate of 5,000 $s^{-1}$. Specifically, such a viscosity is stable during storage for at least three months at 40° C. and 20% relative humidity, in particular the viscosity will not have a more than 50% decrease. More specifically, the return to viscosity at rest after shear is very quick, specifically at most a few minutes, in order to avoid the static leakage in the minutes after writing.

For the purposes of the present invention, the term "fixed color" is intended to mean that the color of the aqueous gel ink by visual observation is the same before application on absorbing support, and after application on an absorbing support, specifically paper, cardboard or textiles, within 7 calendar days (one week).

As indicated above, the aqueous gel ink with fixed color of the invention is obtained by mixing a gel-based matrix of aqueous ink with an aqueous suspension of gold or silver nanoparticles. The aqueous gel ink comprises water and may comprise at least one of a co-solvent, an antimicrobial agent, a corrosion inhibitor, an antifoam agent and a rheology modifier. When present, these ingredients are advantageously added during the preparation of the gel-based matrix of aqueous ink in step (i) of the process of the invention. The aqueous gel ink may further comprise one or more additives selected from pH regulators such as sodium hydroxide and triethanolamine; lubricants; coalescing agents; crosslinking agents; wetting agents; plasticizers; antioxidants, and UV stabilizers. When present, these additives are added during the preparation of the gel-based matrix of aqueous ink in step (i) of the process of the invention.

The aqueous gel ink is prepared by a process well-known by those skilled in the art such as by simple mixing of its ingredients. The overall process of the invention (i.e. steps (i) to (iii)) can generally be performed over a wide range of temperatures. Typically, the process is performed within the temperature range of 0 to 100° C., specifically 5 to 70° C., and more specifically 10 to 40° C. The relatively low process temperatures contribute to process efficiency and process economy, and additionally meet the current ecological demands. Indeed, the process of the invention is performed in aqueous media, and is therefore a "green process". In addition, lower temperatures have the advantage that more stable dispersions are obtained and the gold or silver nanoparticles exhibit better redispersibility.

In one embodiment, the aqueous gel ink comprises a co-solvent and the co-solvent is specifically a polar solvent miscible in water, more specifically a co-solvent selected from:

glycol ethers such as triethylene glycol, polyethylene glycol, diethylene glycol monoethyl ether, diethyleneglycol-mono butyl ether, dipropyleneglycol monobutyl ether, tripropylene glycol monomethyl ether, phenoxyethanol, phenoxypropanol;

alcohols, specifically $C_1$-$C_{15}$ linear or branched alcohols such as isopropanol, butanol, isobutanol, pentanol, benzyl alcohol, glycerin, diglycerin, polyglycerin;

esters such as ethyl acetate or propyl acetate;
carbonate esters such as propylene carbonate or ethylene carbonate;
ketones such as methylisobutylketone (MIBK), acetone or cyclohexanone; and
mixtures thereof.

In one embodiment, the co-solvent is a glycol ether, and is more specifically selected from triethylene glycol, polyethylene glycol, diethylene glycol monoethyl ether, diethylene-glycol-mono butyl ether, dipropyleneglycol monobutyl ether, tripropylene glycol monomethyl ether, phenoxyethanol, phenoxypropanol, and mixture thereof. In a further advantageous embodiment the co-solvent is selected from triethylene glycol, polyethylene glycol and mixture thereof.

The amount of co-solvent (when present) in the aqueous gel ink is in the range from about 5 to about 35%, more specifically from about 9 to about 30%, and even more specifically from about 11 to about 25% by weight, by weight relative to the total weight of the aqueous gel ink.

In one embodiment, the aqueous gel ink comprises an antimicrobial agent, and the antimicrobial agent is specifically an isothiazolinone, more specifically selected from 1,2-benzisothiazolin-3-one, 2-methyl-4-isothiazolin-3-one, and mixtures thereof.

The amount of antimicrobial agent (when present) in the aqueous gel ink is in the range from about 0.01 to about 0.5%, and more specifically from about 0.1 to about 0.2% by weight relative to the total weight of the aqueous gel ink.

In one embodiment, the aqueous gel ink comprises a corrosion inhibitor, and the corrosion inhibitor is specifically selected from tolytriazole, benzotriazole, and mixtures thereof.

The amount of corrosion inhibitor (when present) in the aqueous gel ink is in the range from about 0.05 to about 1%, more specifically from about 0.07 to about 0.5%, and even more specifically from about 0.08 to about 0.15% by weight relative to the total weight of the aqueous gel ink.

In one embodiment, the aqueous ink comprises an antifoam agent, and the antifoam agent is specifically a polysiloxane-based antifoam agent, and more specifically an aqueous emulsion of modified polysiloxane (such as MOUSSEX® from Synthron, TEGO® Foamex from Evonik).

The amount of antifoam agent (when present) in the aqueous gel ink is in the range from about 0.05 to about 1%, more specifically from about 0.1 to about 0.5%, and even more specifically from about 0.2 to about 0.4% by weight relative to the total weight of the aqueous gel ink.

In one embodiment, the aqueous ink comprises a rheology modifier capable of generating a gelling effect, and the rheology modifier can be specifically a polysaccharide such as xanthan gum, gum arabic, and mixtures thereof.

The amount of rheology modifier (when present) in the aqueous gel ink is in the range from about 0.08 to about 2%, more specifically from about 0.2 to about 0.8%, and even more specifically from about 0.3 to about 0.6% by weight relative to the total weight of the aqueous gel ink.

In one embodiment, the aqueous gel ink does not contain any reducing agent or any oxidizing agent. The aqueous suspension prepared in step (ii) of the process of the invention comprises, in addition to water, gold or silver nanoparticles, at least one derivative of alkaline earth metal, an ester of retinol of formula (I) and optionally a carbonate.

The gold or silver nanoparticles are typically obtained by reaction of a gold salt (respectively, silver salt) with a reducing agent. In one embodiment, the gold salt is $HAuCl_4$, optionally in the form of the trihydrate. In one embodiment, the silver salt is at least one of $AgNO_3$, $AgClO_4$, $Ag_2SO_4$, AgCl, AgBr, AgOH, $Ag_2O$, $AgBF_4$, $AgIO_3$ and $AgPF_6$, more specifically the silver salt is $AgNO_3$, in particular an aqueous solution of $AgNO_3$.

In one embodiment, the total amount of gold or silver salt in the aqueous suspension ranges from about 0.05 to about 1% by weight, specifically from about 0.01 to about 0.05% by weight, based on the total weight of the aqueous suspension.

Gold or silver nanoparticles are formed when the gold or silver salt is contacted with the reducing agent.

The reducing agent comprises a derivative of alkaline earth metal, an ester of retinol of formula (I) and optionally a carbonate.

In one embodiment, the derivative of alkaline earth metal is an alkaline earth metal halide, specifically an alkaline earth metal chloride, more specifically magnesium or calcium chloride, even more specifically magnesium chloride.

In one embodiment, the total amount of alkaline earth metal derivative in the aqueous suspension ranges from about 0.01 to about 0.1% by weight, specifically from about 0.02 to about 0.08% by weight, based on the total weight of the aqueous suspension.

The ester of retinol is a compound of formula (I):

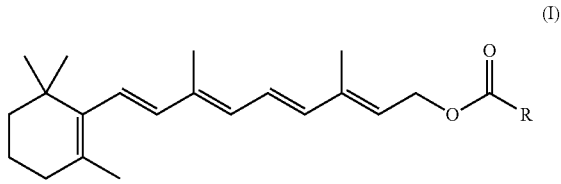

(I)

wherein R is an optionally substituted $C_1$-$C_6$ aliphatic group.

In one embodiment, the aliphatic group is an alkyl group, specifically a $(C_1$-$C_6)$alkyl group, more specifically a $(C_1$-$C_4)$alkyl group, even more specifically a methyl group.

In one embodiment, the substituent of the aliphatic group is at least one of hydroxy, halogen, amino, $(C_1$-$C_3)$alkyl and/or $(C_1$-$C_3)$alkoxy.

In one embodiment, the total amount of ester of retinol in the aqueous suspension ranges from about 0.5 to about 5% by weight, specifically from about 1 to about 4% by weight, based on the total weight of the aqueous suspension.

In one embodiment, the carbonate is an alkali metal or alkaline earth metal carbonate, specifically at least one of potassium carbonate, sodium carbonate, magnesium carbonate, calcium carbonate, strontium carbonate, barium carbonate, and mixtures thereof, more specifically at least one of magnesium carbonate, calcium carbonate, strontium carbonate and barium carbonate, even more specifically calcium carbonate.

In one embodiment, the total amount of carbonate in the aqueous suspension ranges from about 0.05 to about 0.2% by weight, specifically from about 0.1 to about 0.15% by weight, based on the total weight of the aqueous suspension.

In one embodiment, the aqueous suspension comprises a carbonate.

The aqueous suspension of gold silver nanoparticles obtained in step (ii) has a fixed color, which color may vary depending on the type of nanoparticles (gold or silver) and the amount of reducing agent used.

In one aspect, the present invention also relates to a process for preparing an aqueous suspension of gold or silver nanoparticles with fixed color according to step (ii) and to the aqueous suspension obtainable according to step (ii).

In one aspect, the present invention also relates to an aqueous gel ink with fixed color obtainable by the process of the invention, as defined above, comprising gold or silver nanoparticles.

In one embodiment, the total amount of water ranges from about 50% to about 95%, specifically from about 60% to about 90%, and more specifically from about 70% to about 85%, by weight relative to the total weight of the aqueous gel ink.

In one embodiment, the total amount of gold or silver nanoparticles in the aqueous ink ranges from about 0.05 to about 5% by weight, specifically from about 0.05 to about 0.5% by weight, more specifically from about 0.07 to about 0.4% by weight, based on the total weight of the aqueous gel ink.

In one embodiment, the gold or silver nanoparticles present in the aqueous gel ink with fixed color of the invention have the shape of spheres or a polyhedral shape, specifically a polyhedral shape.

In the aqueous gel ink with fixed color of the invention, the gold or silver nanoparticles of the invention have specifically an average particle size ranging from about 10 to about 200 nm and more specifically from about 50 to about 150 nm. This average particle size is determined by analysis of 2D images (microscope: JEOL ARM 200), according to the standard ISO9001:2015.

In one embodiment, after writing onto absorbing support with the aqueous gel ink of fixed color of the invention, the distance between gold or silver nanoparticles within the aqueous gel ink applied on absorbing support is lower than 3 μm, specifically from 100 nm to 2 μm and more specifically from 500 nm to 1.5 μm.

More specifically, the aqueous ink with fixed color of the disclosure and the aqueous suspension of gold or silver nanoparticles obtained in step (ii) comprise alkaline earth metal salt, more specifically magnesium or calcium salts.

The fixed color of the aqueous gel ink of the invention will be the same as the fixed color of the aqueous suspension of gold or silver nanoparticles obtained in step (ii). Therefore specifically the gold or silver nanoparticles are the only coloring agent of the aqueous gel ink of the invention. In this case, the aqueous gel ink according to the invention does not contain any coloring agent other than the gold or silver nanoparticles.

In one aspect, the invention relates to a process for preparing an aqueous ink with fixed color, comprising the following steps:
 (i) preparing a matrix of aqueous ink ;
 (ii) preparing an aqueous suspension of gold or silver nanoparticles with fixed color by mixing gold or silver salts with:
  water,
  a derivative of alkaline earth metal,
  an ester of retinol of formula (I):

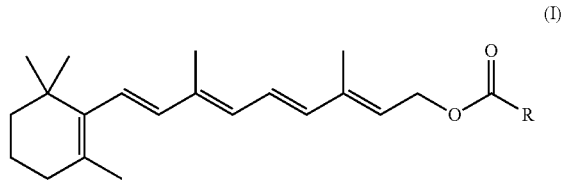

wherein R is an optionally substituted $C_1$-$C_6$ aliphatic group, specifically a ($C_1$-$C_6$)alkyl group, and
 optionally, a carbonate;
 (iii) adding under stirring the aqueous suspension of gold or silver nanoparticles obtained in step (ii) to the matrix of aqueous ink obtained in step (i), thereby obtaining an aqueous ink with fixed color with gold or silver nanoparticles dispersed therein.

In one aspect, the invention also relates to an aqueous ink with fixed color obtainable according to above-mentioned process, in particular comprising gold or silver nanoparticles dispersed therein, in particular which are as defined in the present disclosure.

The aqueous ink with fixed color of the invention may also comprise classic ink ingredients as described previously, such as solvents, antimicrobial agents, corrosion inhibitors, antifoam agents, rheology modifiers. These ingredients are added to the matrix of aqueous ink in step (i) of the process of the invention.

In one aspect, the invention relates to the use of the aqueous ink of fixed color, more specifically of the aqueous gel ink of fixed color, as defined above for writing onto an absorbing support. In one embodiment, the absorbing support is a porous substrate, specifically paper, cardboard, or textiles.

In one aspect, the invention relates to a method of writing comprising writing onto an absorbing support, specifically as defined above, with an aqueous ink with fixed color, more specifically an aqueous gel ink with fixed color, according to the invention.

In one aspect, the invention relates to a writing instrument comprising:
 an axial barrel containing the aqueous ink, more specifically the aqueous gel ink, according to the invention, and
 a pen body which delivers the aqueous ink, more specifically the aqueous gel ink, stored in the axial barrel.

In one embodiment, the writing instrument is selected from gel pens, felt pens, correction fluid, markers, specifically gel pens.

The present invention therefore relates to a process for preparing an aqueous ink wherein preparing a matrix of aqueous ink in step (i). The present invention therefore also relates to an aqueous ink that is obtainable through such process. The various embodiments described here before regarding the process of preparation of an aqueous gel ink and regarding the aqueous gel ink that can be obtained through this process can be as well considered for the process of preparation of the aqueous ink and for the aqueous ink thus obtained, in particular regarding the nature and/or content of the components. These embodiments regarding the aqueous ink, its process of preparation and the matrix of aqueous ink are also part of the present invention.

The invention will be better understood in the light of the following examples given by way of illustration only.

EXAMPLE 1

Preparation of an Aqueous Gel Ink with Fixed Color Based on Vitamin A Acetate and Gold Nanoparticles, According to the Process of the Invention A gel-based matrix of aqueous ink was prepared by mixing 15 g of triethylene glycol (solvent), 4 g of polyethylene glycol (solvent), 0.19 g of Acticide® MBS (antimicrobial agent), and 0.10 g of Additin® RC8221 (corrosion inhibitor). The mixture was homogenised with a homogenizer mixer at a speed of 15 m·s$^1$ during 15 minutes and heated at a temperature of 35° C. Then, 0.4 g of xanthan gum (rheology modifier) was added to the mixture. The mixture was homogenized with a homogenizer mixer at a speed of 15 m·s$^{-1}$ during 15 minutes at a temperature of 35° C. 80.01 g of deionized water were slowly added to the mixture. The mixture was left to stand for 2 h30. Then, 0.3 g of Moussex® S 9092 (antifoam agent) was added. The mixture was homogenized with a homogenizer mixer at a speed of 15 m·s$^{-1}$ during 30 minutes at a temperature of 35° C. The gel-based matrix of aqueous ink obtained was cooled at room temperature (25° C.).

In a separate step, 1 mL of distilled water was mixed with 0.025 g of vitamin A acetate (trade name: Retinyl acetate Sigma Aldrich). The mixture was homogenized with a homogenizer mixer at a speed of 400 rpm during 5 minutes. 50 µL of a solution of magnesium chloride (100 mM) (magnesium chloride anhydrous—Merck) and 100 µL of a solution of calcium carbonate (150 mM) (calcium carbonate—Prolabo) were added to the mixture, which was homogenized at a speed of 400 rpm during 5 minutes.

Then, 50 µL of a solution of gold (III) chloride trihydrate (520918-1G Sigma-Aldrich) (200 mM) were added to the mixture stirred at a speed of 400 rpm during 10 minutes. When the (continuous) addition of the solution of gold (III) chloride trihydrate was complete, a brown aqueous suspension was obtained.

The aqueous suspension of gold nanoparticles obtained was then mixed with the gel-based matrix of aqueous ink to obtain an aqueous gel ink with fixed color (brown color) with gold nanoparticles dispersed therein.

When the obtained aqueous gel ink with fixed color was written on cellulosic paper, a brown color instantly appeared. Furthermore, a visual assessment of the color of the aqueous gel ink was realized over time. As can be seen from Table 1, the color of the aqueous gel ink did not change over time.

TABLE 1

| Time | 0 min | 2 min | 1 hour | 1 day | 1 week |
|---|---|---|---|---|---|
| Color of the aqueous gel ink before application on cellulosic paper | Brown | Brown | Brown | Brown | Brown |
| Color of the aqueous gel ink after application on cellulosic paper | Brown | Brown | Brown | Brown | Brown |

EXAMPLE 2

Preparation of an Aqueous Gel Ink with Fixed Color Based on Vitamin A Acetate and Silver Nanoparticles, According to the Process of the Present Invention A gel-based matrix of aqueous ink was prepared by mixing 15 g of triethylene glycol (solvent), 4 g of polyethylene glycol (solvent), 0.19 g of Acticide® MBS (antimicrobial agent), and 0.10 g of Additin® RC8221 (corrosion inhibitor). The mixture was homogenized with a homogenizer mixer at a speed of 15 m·s$^{-1}$ during 15 minutes and heated at a temperature of 35° C. Then, 0.4 g of xanthan gum (rheology modifier) was added to the mixture. The mixture was homogenized with a homogenizer mixer at a speed of 15 m·s$^{-1}$ during 15 minutes at a temperature of 35° C. 80.01 g of deionized water were slowly added to the mixture. The mixture was left to stand for 2 h30. Then, 0.3 g of Moussex® S 9092 (antifoam agent) was added. The mixture was homogenized with a homogenizer mixer at a speed of 15 m·s$^{-1}$ during 30 minutes at a temperature of 35° C. The gel-based matrix of aqueous ink obtained was cooled at room temperature (25° C.).

In a separate step, 1 mL of distilled water was mixed with 0.025g of vitamin A acetate (trade name: Retinyl acetate Sigma Aldrich). The mixture was homogenized with a homogenizer mixer at a speed of 400 rpm during 5 minutes. 50 µL of a solution of magnesium chloride (100 mM) (magnesium chloride anhydrous—Merck) and 100 µL of a solution of calcium carbonate (150 mM) (calcium carbonate—Prolabo) were added to the mixture, which was homogenized at a speed of 400 rpm during 5 minutes.

Then, 50 µL of a solution of silver nitrate (200 mM) was introduced into the mixture stirred at a speed of 400 rpm during 10 minutes. When the (continuous) addition of the solution of silver nitrate was complete, a dark aqueous suspension was obtained.

The aqueous suspension of silver nanoparticles obtained was then mixed with the gel-based matrix of aqueous ink to obtain an aqueous gel ink with fixed color (dark brown color) with silver nanoparticles dispersed therein.

When the obtained aqueous gel ink with fixed color was written on cellulosic paper, a dark brown color instantly appeared. Furthermore, a visual assessment of the color of the aqueous gel ink was realized over time. As can be seen from Table 2 the color of the aqueous gel ink did not change over time.

TABLE 2

| Time | 0 min | 2 min | 1 hour | 1 day | 1 week |
|---|---|---|---|---|---|
| Color of the aqueous gel ink before application on the cellulosic paper | Dark Brown | Dark Brown | Dark Brown | Dark Brown | Dark Brown |
| Color of the aqueous gel ink after application on the cellulosic paper | Dark Brown | Dark Brown | Dark Brown | Dark Brown | Dark Brown |

COMPARATIVE EXAMPLE 1

Preparation of an Aqueous Gel Ink Comprising Gold Nanoparticles

A gel-based matrix of aqueous ink was prepared by mixing 15 g of triethylene glycol (solvent), 4 g of polyethylene glycol (solvent), 0.19 g of Acticide® MBS (antimicrobial agent), and 0.10 g of Additin® RC8221 (corrosion inhibitor). The mixture was homogenized with a homogenizer mixer at a speed of 15 m·s$^{-1}$ during 15 minutes and heated at a temperature of 35° C. Then, 0.4 g of xanthan gum (rheology modifier) was added to the mixture. The mixture was homogenized with a homogenizer mixer at a speed of 15 m·s$^{-1}$ during 15 minutes at a temperature of 35° C. 80.01 g of deionized water was slowly added to the mixture. The mixture was left to stand for 2h30. Then, 0.3 g of Moussex® S 9092 (antifoam agent) was added. The mixture was homogenized with a homogenizing mixer at a speed of 15 m·s$^{-1}$ during 30 minutes at a temperature of 35° C. The gel-based matrix of aqueous ink obtained was cooled at room temperature (25° C.).

50 µL of a solution of magnesium chloride (100 mM) (magnesium chloride anhydrous—Merck) were added to the mixture, which was stirred at a speed of 400 rpm during 5 minutes.

Then, 50 µL of a solution of gold (III) chloride trihydrate (520918-1G Sigma-Aldrich) (200 mM) were introduced into the mixture stirred at a speed of 400 rpm during 10 minutes. When the (continuous) addition of the solution of gold (III) chloride trihydrate was complete, an opaque aqueous suspension was obtained.

The aqueous suspension of gold nanoparticles obtained was then mixed with the gel-based matrix of aqueous ink to obtain an opaque aqueous gel ink with gold nanoparticles dispersed therein.

When the obtained aqueous gel ink with fixed color was written on cellulosic paper, the color did not change and remained opaque. The color could not be seen on the paper.

The invention claimed is:

1. A process for preparing an aqueous gel ink with fixed color comprising the steps of:
   (i) preparing a gel-based matrix of aqueous ink;
   (ii) preparing an aqueous suspension of gold or silver nanoparticles with fixed color by mixing gold or silver salts with:
      water,
      a derivative of alkaline earth metal,
      an ester of retinol of formula (I):

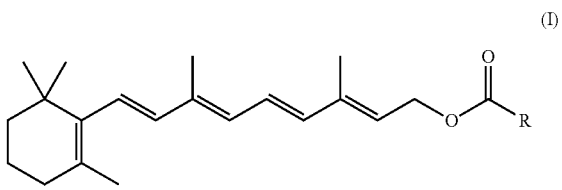

wherein R is an optionally substituted $C_1$-$C_6$ aliphatic group, and
      optionally, a carbonate;
   (iii) adding under stirring the aqueous suspension of gold or silver nanoparticles obtained in step (ii) to the gel-based matrix of aqueous ink obtained in step (i), thereby obtaining an aqueous gel ink with fixed color with gold or silver nanoparticles dispersed therein.

2. The process according to claim 1, wherein the total amount of gold or silver salts in the aqueous suspension is in range from 0.05 to 1% by weight, based on the total weight of the aqueous suspension.

3. The process according to claim 1, wherein the derivative of alkaline earth metal is an alkaline earth metal halide.

4. The process according to claim 1, wherein the total amount of alkaline earth metal derivative in the aqueous suspension is in the range from 0.01 to 0.1% by weight, based on the total weight of the aqueous suspension.

5. The process according to claim 1, wherein the total amount of ester of retinol in the aqueous suspension is in the range from 0.5 to 5% by weight, based on the total weight of the aqueous suspension.

6. The process according to claim 1, wherein the carbonate is an alkali metal or alkaline earth metal carbonate.

7. The process according to claim 1, wherein the total amount of carbonate in the aqueous suspension is in the range from 0.05 to 0.2% by weight, based on the total weight of the aqueous suspension.

8. The process according to claim 1, wherein the gold or silver nanoparticles obtained in step (ii) have a spherical or polyhedral shape, and/or wherein the gold or silver nanoparticles obtained in step (ii) have an average particle size ranging from 10 to 200 nm.

9. The aqueous gel ink with fixed color obtained by the process according to claim 1, comprising gold or silver nanoparticles dispersed therein.

10. The aqueous gel ink according to claim 9, wherein the aqueous gel ink does not contain any other coloring agent than the silver or gold nanoparticles.

11. The aqueous gel ink according to claim 9, wherein the total amount of water ranges from 50 to 95% by weight relative to the total weight of the aqueous gel ink.

12. The aqueous gel ink according to claim 9, wherein the total amount of gold or silver nanoparticles in the aqueous gel ink is in the range from 0.05 to 5% by weight, based on the total weight of the aqueous gel ink.

13. The aqueous gel ink according to claim 9, further comprising:
   a co-solvent, in an amount ranging from 5 to 35% by weight relative to the total weight of the aqueous gel ink; and/or
   an antimicrobial agent, in an amount ranging from 0.01 to 0.5% by weight relative to the total weight of the aqueous gel ink, and/or
   a corrosion inhibitor, in an amount ranging from 0.5 to 1% by weight relative to the total weight of the aqueous gel ink; and/or
   an antifoam agent, in an amount ranging from 0.05% to 1% by weight relative to the total weight of the aqueous gel ink; and/or
   a rheology modifier, in an amount ranging from 0.08 to 0.2% by weight relative to the total weight of the aqueous gel ink.

14. A writing instrument comprising:
   an axial barrel containing an aqueous gel ink with fixed color according to claim 9, and
   a pen body which delivers the aqueous gel ink stored in the axial barrel,
   wherein the writing instrument is chosen in the group consisting of gel pens, felt pens, correction fluid and markers.

15. The writing instrument according to claim 14, wherein the writing instrument is chosen in the group consisting of gel pens.

16. The aqueous gel ink according to claim 9, wherein the total amount of gold or silver nanoparticles in the aqueous gel ink is in the range from 0.05 to 0.5% by weight, based on the total weight of the aqueous gel ink.

17. The process according to claim 1, wherein R is an optionally substituted ($C_1$-$C_6$) alkyl group.

18. The process according to claim 1, wherein the derivative of alkaline earth metal is an alkaline earth metal chloride.

19. The process according to claim 1, wherein the derivative of alkaline earth metal is magnesium or calcium chloride.

* * * * *